(12) United States Patent
Christensen

(10) Patent No.: US 10,288,881 B2
(45) Date of Patent: May 14, 2019

(54) WEARABLE INTERFACE FOR REMOTE MONITORING AND CONTROL OF A MEDICAL DEVICE

(71) Applicant: Fresenius Medical Care Holdings, Inc., Waltham, MA (US)

(72) Inventor: Peter Christensen, Concord, CA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 116 days.

(21) Appl. No.: 13/804,761

(22) Filed: Mar. 14, 2013

(65) Prior Publication Data

US 2014/0266983 A1 Sep. 18, 2014

(51) Int. Cl.
*G06F 3/01* (2006.01)
*G06K 9/00* (2006.01)
(Continued)

(52) U.S. Cl.
CPC .......... *G02B 27/017* (2013.01); *A61M 1/1601* (2014.02); *A61M 1/34* (2013.01);
(Continued)

(58) Field of Classification Search
CPC .......... G06F 3/017; G06F 21/00; G06F 15/16; G06F 3/00; G06F 3/01; G06F 3/033;
(Continued)

(56) References Cited

U.S. PATENT DOCUMENTS 6,057,966 A 5/2000 Carroll et al.
6,349,001 B1 2/2002 Spitzer
(Continued)

FOREIGN PATENT DOCUMENTS

DE 198 45 027 C2 4/2000
DE 10 2004 011 264 A1 9/2004
(Continued)

OTHER PUBLICATIONS

Fresenius Medical Care, "2008T Hemodialysis Machine Operator's Manual," P/N 490122 Rev I, May 9, 2012, 222 pp.
(Continued)

*Primary Examiner* — Chanh D Nguyen
*Assistant Examiner* — Nguyen H Truong
(74) *Attorney, Agent, or Firm* — Muirhead and Saturnelli, LLC

(57) ABSTRACT

A wearable interface device, such as a head-mounted display, provides an augmented reality and/or display system and may be used in accordance with medical devices and the performance of medical treatments, particularly a dialysis machine and a dialysis treatment. The wearable interface device may be worn by a user, such as a health care practitioner (HCP), in connection with remotely monitoring and/or controlling the dialysis machine during the dialysis treatment. The HCP may receive alerts and/or other information concerning the dialysis treatment from the dialysis machine that are displayed on the wearable interface device and may use the wearable interface device to control the dialysis machine via the exchange of wireless signals with the dialysis machine. The wearable interface device may recognize commands from the HCP, such as gestures, to provide non-contact operation of the wearable interface device and remote control of the dialysis machine by the HCP.

22 Claims, 12 Drawing Sheets

(51) Int. Cl.
  *G02B 27/01* (2006.01)
  *A61M 1/16* (2006.01)
  *A61M 1/36* (2006.01)
  *A61M 1/34* (2006.01)
  *G16H 40/63* (2018.01)
  *G06F 19/00* (2018.01)

(52) U.S. Cl.
  CPC ........ *A61M 1/3403* (2014.02); *A61M 1/3607* (2014.02); *A61M 1/3609* (2014.02); *G06F 19/00* (2013.01); *G16H 40/63* (2018.01); *A61M 2205/3368* (2013.01); *A61M 2205/3561* (2013.01); *A61M 2205/3592* (2013.01); *A61M 2205/50* (2013.01); *A61M 2205/502* (2013.01); *A61M 2205/505* (2013.01); *A61M 2205/507* (2013.01); *G02B 2027/014* (2013.01); *G02B 2027/0178* (2013.01); *G02B 2027/0187* (2013.01)

(58) Field of Classification Search
  CPC ........ G06F 3/048; G06F 17/00; G02B 27/01; G02B 27/017; G02B 2207/0138; G09G 9/00; G09G 9/40; G09G 5/00; G09G 5/377; G06Q 30/00; H04N 5/225; H04N 5/228; H04N 13/00; H04N 13/02; H04L 29/06; G06T 15/00; G06T 15/20; G06T 13/00; G06T 7/00; H03G 3/00; G01C 21/00
  USPC .......................................... 345/7–9, 156, 157
  See application file for complete search history.

(56) References Cited

U.S. PATENT DOCUMENTS

| | | |
|---|---|---|
| 6,409,661 B1 | 6/2002 | Murphy |
| 6,775,577 B2 | 8/2004 | Crnkovich et al. |
| 6,847,336 B1 | 1/2005 | Lemelson et al. |
| 7,078,911 B2 | 7/2006 | Cehelnik |
| 7,539,533 B2 | 5/2009 | Tran |
| 7,794,419 B2 | 9/2010 | Paolini et al. |
| 7,857,756 B2 | 12/2010 | Warren et al. |
| 7,896,869 B2 | 3/2011 | DiSilvestro et al. |
| 7,922,899 B2 | 4/2011 | Vasta et al. |
| 7,973,667 B2 | 7/2011 | Crnkovich et al. |
| 7,988,849 B2 | 8/2011 | Biewer et al. |
| 8,043,224 B2 | 10/2011 | Sarel |
| 8,110,104 B2 | 2/2012 | Crnkovich et al. |
| 8,212,859 B2 | 7/2012 | Tang et al. |
| 8,223,088 B1 | 7/2012 | Gomez et al. |
| 8,228,315 B1 | 7/2012 | Starner et al. |
| 8,321,044 B2 | 11/2012 | Plahey et al. |
| 8,323,503 B2 | 12/2012 | Levin et al. |
| 8,487,881 B2 | 7/2013 | Keenan |
| 8,508,472 B1* | 8/2013 | Wieder ............... 345/156 |
| 8,558,759 B1* | 10/2013 | Prada Gomez ......... G06F 3/017 345/156 |
| 8,606,595 B2 | 12/2013 | Udani |
| 8,655,796 B2 | 2/2014 | Udani |
| 8,690,155 B2 | 4/2014 | Riley |
| 8,970,503 B2 | 3/2015 | Christie et al. |
| 9,042,596 B2 | 5/2015 | Connor |
| 9,224,180 B2 | 12/2015 | Macoviak et al. |
| 9,344,612 B2 | 5/2016 | Ritchey et al. |
| 9,427,305 B2 | 8/2016 | Kuraguntla et al. |
| 9,697,556 B2 | 7/2017 | Mazed et al. |
| 9,727,042 B2 | 8/2017 | Hoffberg-Borghesani et al. |
| 9,805,624 B2 | 10/2017 | Reihsen et al. |
| 9,826,903 B2 | 11/2017 | Derchak |
| 9,907,730 B2 | 3/2018 | Macoviak et al. |
| 9,936,906 B2 | 4/2018 | Satish et al. |
| 2003/0093300 A1* | 5/2003 | Denholm ............. G06F 3/0219 705/2 |
| 2003/0128125 A1 | 7/2003 | Burbank et al. |
| 2004/0193413 A1 | 9/2004 | Wilson et al. |
| 2004/0220832 A1 | 11/2004 | Moll et al. |
| 2006/0181482 A1 | 8/2006 | Iaquinto |
| 2006/0200260 A1 | 9/2006 | Hoffberg et al. |
| 2007/0112603 A1 | 5/2007 | Kauthen et al. |
| 2007/0191070 A1 | 8/2007 | Rao |
| 2008/0082363 A1 | 4/2008 | Habashi |
| 2008/0114226 A1* | 5/2008 | Music et al. ............. 600/323 |
| 2009/0076856 A1* | 3/2009 | Darby ............... A61M 1/16 705/3 |
| 2009/0222119 A1 | 9/2009 | Plahey et al. |
| 2009/0259960 A1 | 10/2009 | Steinle et al. |
| 2009/0265188 A1 | 10/2009 | Lamy et al. |
| 2009/0275881 A1 | 11/2009 | Lo et al. |
| 2009/0294339 A1 | 12/2009 | Biewer et al. |
| 2009/0299645 A1 | 12/2009 | Colby et al. |
| 2009/0306573 A1 | 12/2009 | Gagner et al. |
| 2010/0066676 A1 | 3/2010 | Kramer et al. |
| 2010/0141554 A1 | 6/2010 | Devereaux et al. |
| 2010/0143192 A1 | 6/2010 | Myrick et al. |
| 2010/0198613 A1 | 8/2010 | Weller et al. |
| 2010/0271296 A1 | 10/2010 | Kopychev |
| 2010/0318578 A1* | 12/2010 | Treu ............... G06F 19/3418 707/802 |
| 2011/0144636 A1 | 6/2011 | Alexander et al. |
| 2011/0157480 A1 | 6/2011 | Curl |
| 2011/0164163 A1 | 7/2011 | Bilbrey et al. |
| 2011/0214162 A1 | 9/2011 | Brakensiek et al. |
| 2011/0221658 A1 | 9/2011 | Haddick et al. |
| 2011/0225000 A1 | 9/2011 | Selim |
| 2011/0307079 A1 | 12/2011 | Oweiss et al. |
| 2012/0035534 A1 | 2/2012 | Yu et al. |
| 2012/0138533 A1* | 6/2012 | Curtis et al. ................ 210/646 |
| 2012/0154264 A1 | 6/2012 | Wang et al. |
| 2012/0212455 A1 | 8/2012 | Kloeffel |
| 2012/0218187 A1* | 8/2012 | Stewart et al. ............. 345/168 |
| 2012/0224060 A1* | 9/2012 | Gurevich ............... B60R 1/00 348/148 |
| 2012/0249797 A1 | 10/2012 | Haddick et al. |
| 2012/0293548 A1 | 11/2012 | Perez et al. |
| 2012/0323590 A1 | 12/2012 | Udani |
| 2012/0323805 A1 | 12/2012 | Udani |
| 2013/0009993 A1* | 1/2013 | Horseman ........... G06F 19/3418 345/633 |
| 2013/0018355 A1 | 1/2013 | Brand et al. |
| 2013/0023910 A1* | 1/2013 | Solomon ............. A61B 5/4887 606/158 |
| 2013/0037485 A1 | 2/2013 | Wilt et al. |
| 2013/0050069 A1* | 2/2013 | Ota ..................... 345/156 |
| 2013/0050432 A1* | 2/2013 | Perez ............... H04N 13/0278 348/47 |
| 2013/0088507 A1* | 4/2013 | White ............... G02B 27/017 345/592 |
| 2013/0117040 A1 | 5/2013 | James et al. |
| 2013/0141313 A1* | 6/2013 | Zhou et al. ..................... 345/8 |
| 2013/0141421 A1* | 6/2013 | Mount ............ H04N 21/41407 345/419 |
| 2013/0184745 A1* | 7/2013 | Leschinsky ........ A61B 5/6831 606/202 |
| 2013/0249855 A1 | 9/2013 | Zhang |
| 2013/0267883 A1 | 10/2013 | Medrano |
| 2014/0243652 A1 | 8/2014 | Pashko |
| 2014/0266983 A1 | 9/2014 | Christensen |
| 2014/0267003 A1 | 9/2014 | Wang et al. |
| 2015/0177864 A1* | 6/2015 | Wong ............... G02B 27/017 345/175 |

FOREIGN PATENT DOCUMENTS

| | | |
|---|---|---|
| DE | 10 2007 006 566 A1 | 8/2008 |
| DE | 10 2011 011 767 A1 | 8/2012 |
| DE | 10 2011 053 935 A1 | 3/2013 |
| DE | 10 2013 111 084 A1 | 4/2015 |
| EP | 2237131 A1 | 10/2010 |
| WO | WO 2008/042219 A2 | 4/2008 |

(56) References Cited

FOREIGN PATENT DOCUMENTS

WO     WO 2011/144747 A1    11/2011
WO     WO 2013/170204 A1    11/2013

OTHER PUBLICATIONS

Martin Tosas et al., "Virtual Touch for Mixed Reality," May 13, 2004, Computer Vision in Human-Computer Interaction, Lecture Notes in Computer Science, Springer-Verlag, Berlin/Heidelberg, pp. 48-59, XP019006108, ISBN 978-3-540-22012-1.

Berührungslose Gestern- und Körpererkennung in der Diagnostik, "Jeder Atemzug wird erkannt," medizin & technic, Jun. 2012, 3 pp., URL: http://www.medizin-und-technik.de/, (with Machine Translation).

Please do not touch, "Berührungslose Interaktion anhand von 3-D Bilddaten," www.inspect-online.com, Inspect Jul. 2011; URL: http://www.gestigon.de/uploads/mediaGestigon_INS0711.pdf, (with Machine Translation).

\* cited by examiner

WEARABLE INTERFACE FOR REMOTE MONITORING AND CONTROL OF A MEDICAL DEVICE

TECHNICAL FIELD

This patent application is related to processing devices and interfaces in the medical device area.

BACKGROUND OF THE INVENTION

Hemodialysis is a process which employs a machine that includes a dialyzer to aid patients whose renal function has deteriorated to the point where their body cannot adequately rid itself of toxins. The dialyzer may include a semi-permeable membrane, the membrane serving to divide the dialyzer into two chambers. Blood is pumped through one chamber and a dialysis solution through the second. As the blood flows by the dialysis fluid, impurities, such as urea and creatinine, diffuse through the semi-permeable membrane into the dialysis solution. The electrolyte concentration of the dialysis fluid may be set so as to maintain electrolytic balance within the patient. Other purification techniques and processes may additionally be used. Hemodialysis may be generally referred to herein as "dialysis," although it is noted that other types of dialysis exist, such a peritoneal dialysis, and it is noted that the system described herein may be used in connection with any appropriate dialysis system or similar treatment system.

Since dialysis involves removing blood from and returning blood to a patient, performing a dialysis procedure carries a degree of risk. Dialysis treatment requires monitoring of several patient vital signs and dialysis parameters during the dialysis process in order to optimize the overall efficacy of the dialysis procedure, to assess the condition of a fistula (the access to the patient's blood) and to determine the actual purification achieved. Some examples of parameters monitored and analyzed by a dialysis machine or equipment include the blood access flow rate or the rate at which blood flows out of the patient to the dialyzer, a critical parameter; and the ratio Kt/V to measure dialysis efficiency, where K is the clearance or dialysance (both terms representing the purification efficiency of the dialyzer), t is treatment time and V is the patient's total water value.

A processing device coupled to the dialysis machine may be used to manage and oversee the functions of the dialysis process and to, for example, monitor, analyze and interpret patient vital signs and dialysis parameters during a dialysis procedure. The processing device may include a display that displays information concerning the dialysis procedure and include an interface that enables configuration and control of the dialysis machine. A health care practitioner such as a nurse or a patient care technician may oversee the dialysis treatment sessions. Data provided by the dialysis machine and the processing device may aid the health care practitioner in performing his or her duties.

For various descriptions of dialysis systems and components, reference is made, for example, to U.S. Pat. No. 8,110,104 B2 to Crnkovich et al., entitled "Dialysis Systems and Related Components," and U.S. Pat. No. 6,775,577 B2 to Crnkovich et al., entitled "Method and System for Controlling a Medical Device," which are incorporated herein by reference. For a description of a sensor system that may be used in connection with monitoring and issuing alerts during a dialysis procedure, reference is made, for example, to U.S. Pat. No. 7,973,667 B2 to Crnkovich et al., entitled "Wetness Sensor," which is incorporated herein by reference. For various descriptions of interfaces for dialysis systems, reference is made, for example, to U.S. Pat. No. 8,323,503 B2 to Levin et al., entitled "User Interface Processing Device" and U.S. Patent App. Pub. No. 2007/0112603 A1 to Kauthen et al., entitled "Digital Data Entry Methods and Devices," which are incorporated herein by reference.

In a clinic environment, there may be one health care practitioner for multiple patients, so it is often the case that while the health care practitioner is helping one patient, an alarm may go off for another patient that requires the health care practitioner to investigate and/or attend. In such cases, the health care practitioner may often need to leave a current duty to go to the source of the alarm. Further, where one or more patients are undergoing a dialysis treatment, the health care practitioner may need to adjust the dialysis machine in response to an alarm and/or alert and, in so doing, may often need to re-glove from any prior patient interaction.

Accordingly, it would be desirable to facilitate improvements in the efficient and effective monitoring and control of a dialysis treatment by a health care practitioner overseeing the dialysis treatment, in particular, to enable remote monitoring and control by the health care practitioner of the dialysis treatment and/or dialysis machine and without requiring the health care practitioner to physically contact or even, in some cases, be physically present at the dialysis machine.

SUMMARY OF THE INVENTION

According to the system described herein, a method of remotely interfacing with a medical device includes providing a wearable interface device that enables remote interfacing with the medical device by a user wearing the wearable interface device. Signals are wirelessly exchanged between the wearable interface device and the medical device. The signals corresponds to a treatment performed using the medical device. At least one of the signals at the wearable interface device is used to generate information corresponding to the treatment performed using the medical device. The information is displayed on a screen of the wearable interface device. The medical device may be a dialysis machine. The method may further include recognizing, at the wearable interface device, at least one non-contact command input by the user. The non-contact command may be used to remotely control the medical device during the treatment. The non-contact command may include a command to remotely control the medical device during the treatment by modifying at least one parameter of the medical device from a position in which the wearable interface device is out of visual line-of-sight of the medical device. The wearable interface device may be a head-mounted device, and the information displayed on the screen of the wearable interface device includes dialysis treatment information. The dialysis treatment information may include an alert concerning the dialysis treatment. The method may further include augmenting a real view through the wearable interface device with information corresponding to the dialysis treatment information.

According further to the system described herein, a non-transitory computer-readable medium stores software that remotely interfaces with a medical device. The software includes executable code that operates a wearable interface device that enables remote interfacing with the medical device by a user wearing the wearable interface device. Executable code is provided that wirelessly exchanges signals between the wearable interface device and the medical device, wherein the signals corresponds to a treatment performed using the medical device. Executable code is provided that processes at least one of the signals at the wearable interface device to generate information corresponding to the treatment performed using the medical device. Executable code is provided that displays the information on a screen of the wearable interface device. The medical device may include a dialysis machine. Executable code may be provided that recognizes, at the wearable interface device, at least one non-contact command input by the user. The non-contact command may be used to remotely control the medical device during the treatment. The non-contact command includes a command to remotely control the medical device during the treatment by modifying at least one parameter of the medical device from a position in which the user is out of visual line-of-sight of the medical device. The wearable interface device may be a head-mounted device, and the information displayed on the screen of the wearable interface device includes dialysis treatment information. The dialysis treatment information may include an alert concerning the dialysis treatment. Executable code may be provided that augments a real view through the wearable interface device with information corresponding to the dialysis treatment information.

According to the system described herein, a system is provided for enabling remote interfacing with a dialysis machine. The system includes at least one sensor of the dialysis machine that receives and transmits signals corresponding to a dialysis treatment performed by the dialysis machine. A wearable interface device is provided that is worn by a user and that is wirelessly coupled to the at least one sensor. The wearable interface device includes at least one processor that processes received signals into information corresponding to the dialysis treatment and transmits signals used to control the dialysis machine. At least one screen is provided that displays the information corresponding to the dialysis treatment. At least one command recognition component is provided that recognizes a non-contact command input by the user to the wearable interface device. A camera may be provided that captures an image being viewed using the wearable interface device. The wearable interface device controls the dialysis machine when the wearable interface device is out of a visual line-of-sight with the dialysis machine during the dialysis treatment. The screen of the wearable interface device may include a head-mounted display, and the wearable interface device may include a non-transitory computer readable medium storing software that enables control of the dialysis machine during the dialysis treatment using at least one dialysis treatment screen displayed on the head-mounted display.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

Figure 1:
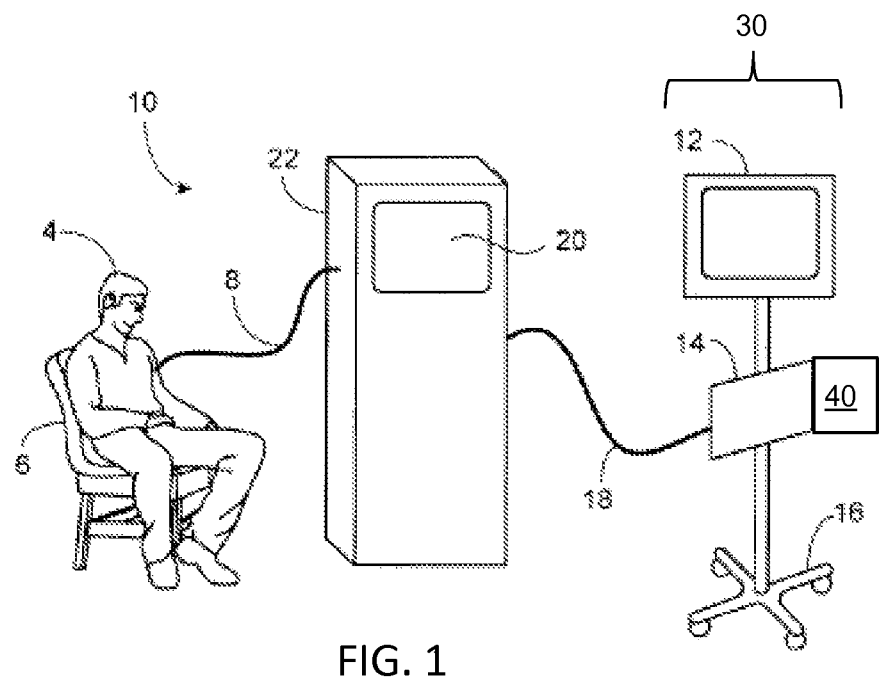
FIG. 1 is a schematic illustration of an example of a patient care environment in which a patient seated in a chair receives medical treatment from a dialysis machine and which may be used in connection with an embodiment of the system described herein.

FIG. 1 is a schematic illustration of an example of a patient care environment 10 in which a patient 4 seated in a chair 6 receives medical treatment from a treatment station 22 and which may be used in connection with an embodiment of the system described herein. The medical treatment is, for example, dialysis. The treatment station 22 may be a dialysis treatment station or dialysis machine. A tube or blood line 8 transports blood from the patient 4 to the dialysis machine 22 and back again to the patient 4 after processing and treatment in the dialysis machine 22. The dialysis machine 22 with display 20 may be connected via cabling 18 to controller device 30 that may include a processor 14 which controls a touch screen display 12. In various embodiments, the display 20 may display information corresponding to a dialysis treatment being performed by the dialysis machine 22. The touch screen display 12 may be mounted on a movable stand 16 of the controller device 30. The touch screen display 12 may include a touch screen that permits a health care practitioner (HCP), such as a nurse, a patient care technician (PCT), or even a patient, to press the display 12 to, for example, to interface with and/or control the dialysis machine 22 and/or to enter patient or other data.

According to various embodiments of the system described herein, a sensor 40 may be coupled to the controller device 30 that may be used to control the dialysis machine 22 in connection with transmitting and/or receiving signals to or from a remote or external interface device, as further discussed in detail elsewhere herein. The sensor 40 may be wirelessly coupled to one or more wireless interface devices that may be used by a PCT to monitor and/or control a dialysis treatment being performed by the dialysis machine 22. Various embodiments for the one or more wireless interface devices and for the actions and functions of the sensor 40 in connection with control of the dialysis machine 22 are further discussed in detail elsewhere herein. It is noted that the system described herein may be used with any appropriate wireless communication technology, including, for example, IEEE 802.11b/g, 802.11b/g/n, and/or Bluetooth, having appropriate security and encryption standards, and used in conjunction with appropriate wireless networks, with hardware and software components, that support such wireless communication technologies.

Figure 2:
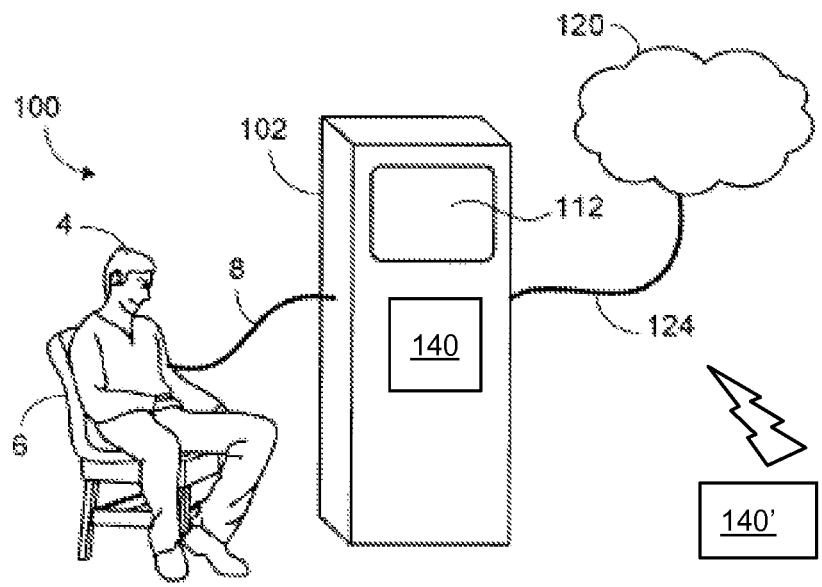
FIG. 2 is a schematic illustration of another example of a patient care environment that may be used in connection with an embodiment of the system described herein.

FIG. 2 is a schematic illustration of another example of a patient care environment 100 that may be used in connection with an embodiment of the system described herein. In the patient care environment 100, the patient 4 is seated in the chair 6 and receives medical treatment from a treatment station, such as a dialysis machine 102. The tube or blood line 8 is used for transporting blood from the patient 4 to the dialysis machine 102 and back again to the patient 4 after processing and treatment of the blood in the dialysis machine 102. The dialysis machine 102 may be configured to communicate with an external network 120, such as a local-area network or the Internet, via a wired or wireless connection 124. The network 120 may include one or more databases or other stores of information that securely contain medical information that may be accessed in connection with operation of the system described herein. It is noted that the system described herein may be used in connection with dialysis products produced by Fresenius Medical Care North America of Waltham, Mass., including, for example, Fresenius hemodialysis systems (e.g., a 2008T system).

In an embodiment, the dialysis machine 102 may include a display 112 with touch screen features. The dialysis machine 102 may centralize and consolidate dialysis functions and data entry functions in a single device 102, without, e.g., the use of a separate, external display (e.g., display 12 of FIG. 1) or a separate, external processor (e.g., processor 14) with associated equipment (e.g., movable stand 16). In an embodiment, the dialysis machine 102 may include one or more processors 114, like the processor 14, that may be used in connection with interfacing with, and control of, the dialysis machine 102, for example, by an HCP during a dialysis treatment. Consolidation of functions in a single dialysis machine 102 may advantageously reduce the amount of external cabling (e.g., cabling 18) to the device 102. The dialysis machine 102 may further reduce the amount of space needed for dialysis treatment and present less crowding of the patient care environment 100. An HCP may be able to focus solely on the dialysis machine 102, or the display 112 of the dialysis machine 102, without the HCP's attention being diverted to, e.g., another external display. The dialysis machine 102 may reduce power consumption and cost as compared to other, non-centralized implementations.

In an embodiment, a sensor 140 may be coupled to the dialysis machine 102. As noted in connection with the sensor 40 of FIG. 1, and as discussed in detail elsewhere herein, the sensor 140 may be used in connection with receiving external or remote signals that may be used to control the dialysis machine 102 and/or may be transmit signals in connection with operation of the dialysis machine 102. In another embodiment, a sensor 140', that may be like the sensor 140, but may be separate from the dialysis machine 140 and coupled wirelessly thereto. Further, the sensor 140' may also be wireless coupled to the network 120. Accordingly, in various embodiments, functions of the sensor 140' may include control of and/or information chance with the dialysis machine 102 via direct communication therewith and/or the sensor 140' may interface with the dialysis machine 102 via the network 120. Further discussions of the features and functions of the sensor 140 and 140' are discussed in detail elsewhere herein.

Figure 3:
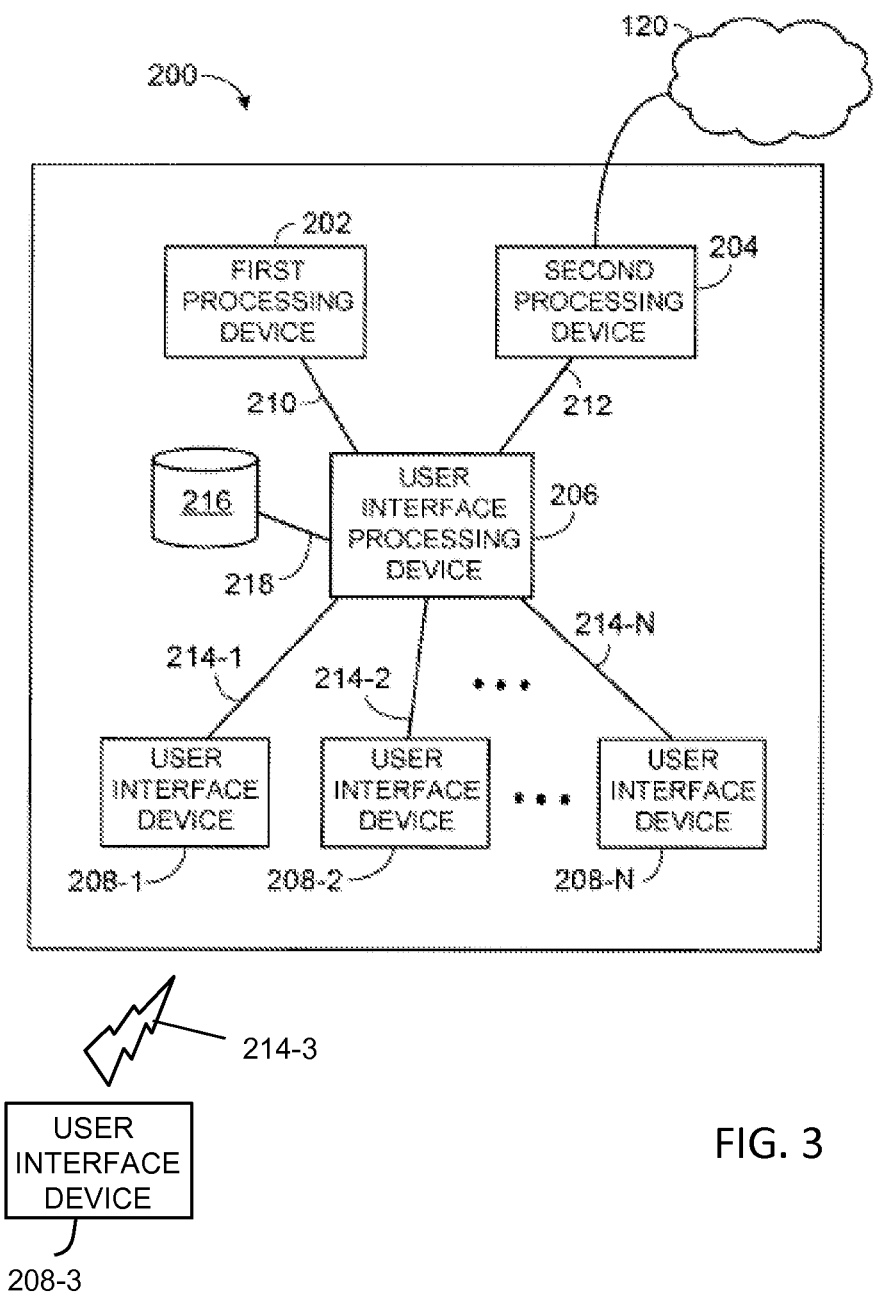
FIG. 3 is schematic illustration of an example implementation of the dialysis machine according to an embodiment of the system described herein.

FIG. 3 is schematic illustration of an example implementation 200 of the dialysis machine 102 according to an embodiment of the system described herein. A user interface processing device (UIP) 206 may be configured to share user interface resources, i.e., user interface devices 208-1, 208-2, 208-3 . . . , 208-N, between a first processing device 202 and a second processing device 204. Both the first and the second processing devices 202, 204 may be connected to the UIP 206 via respective connections 210, 212, while the user interface devices 208-1, 208-2, 208-3 . . . , 208-N are connected to the UIP 206 via connections 214-1, 214-2, 214-3 . . . , 214-N. Although one UIP 206 is shown in FIG. 3, several user interface processing devices may be used to implement the functionality of the UIP 206. The UIP 206 is connected to memory 216 via a connection 218. Other memory (not shown) may be connected to, and, used by, e.g., the first processing device 202 and/or the second processing device 204.

The user interface devices 208-1, 208-2, 208-3 . . . , 208-N may include any of a variety of user interface devices known in the art, such as an alphanumeric keyboard or a keypad, a pointing device (e.g., a touchpad, a mouse, or a trackball), a display, and a display with a touch screen. In an implementation, one or more of the user interface devices 208-1, 208-2, 208-3 . . . , 208-N may be located external to the HD device 200, specifically user interface device 208-3 is shown remotely located and wirelessly coupled, via wireless connection 214-3, to the HD device 200. Various embodiments for a user interface device, like that of user interface device 208-3, being used to wirelessly monitor and/or control the dialysis machine 102 are further discussed in detail elsewhere herein.

The second processing device 204 of the HD device 200 may be configured to communicate with the external network 120, such as a local-area network or the Internet, via a wired or wireless connection 124 (and, e.g., via a network interface (not shown)). In other implementations, other processing devices such as the UIP 206 or the first processing device 202 may communicate with an external network such as the external network 120.

As described herein, the UIP 206 may be configured to share the user interface devices 208-1, 208-2, 208-3 . . . , 208-N between the first processing device 202 and the second processing device 204. The UIP 206 may switch focus from the first processing device 202 to the second processing device 204. The UIP 206 may likewise switch focus from the second processing device 204 to the first processing device 202. Specifically, a processing device, such as the first or the second processing device 202, 204 of FIG. 3, may be said to have focus when the processing device has control of, and/or is controlled by, one or more user interface devices connected to, or communicating with, the processing device (e.g., via one or more user interface processing devices). That is, in this example, when a processing device has focus, a user interface device connected to, or communicating with, the processing device (e.g., via one or more user interface processing devices) will generally affect operation of the processing device, and thereby the dialysis machine 102. User interactions with a user interface device will likewise generally affect operation of the processing device in this instance. Likewise, in this example, when a processing device has focus, the processing device may control a user interface device (such as a video display) connected to, or communicating with, the processing device (e.g., via one or more user interface processing devices).

When a processing device, such as the first or the second processing device 202, 204 of FIG. 3, does not have focus, then, for example, the processing device may not have control of and/or be controlled by one or more user interface devices connected to, or communicating with, the processing device (e.g., via one or more user interface processing devices). Rather, another processing device may have been given focus. One or more user interface processing devices such as the UIP 206 may send protocol data to the processing device, even when the processing device does not presently have focus, so that the processing device may be configured to maintain connections with one or more user interface devices. That is, from the perspective of the processing device, even when the processing device does not have focus, the processing device may have a connection maintained with a user interface device that the processing device does not control and/or that is not controlled by the processing device when the processing device does not have focus. The UIP 206 may therefore send protocol data related to the one or more user interface devices to the first and the second processing devices 202, 204, irrespective of which processing device 202, 204 has focus.

When a processing device (such as the first processing device 202 or the second processing device 204) has focus, one or more user interface processing devices (such as the UIP 206) may manage communications between one or more user interface devices (such as the user interface devices 208-1, 208-2, 208-3 . . . , 208-N) and the processing device. The UIP 206 may, when the processing device has focus, permit the user interface devices 208-1, 208-2, 208-3 . . . , 208-N to affect operation of the processing device. The UIP 206 may switch between modes. The modes may be exclusive of one another and may include a mode in which the first processing device 202 has focus, and a mode in which a second processing device 204 has focus.

According to various embodiments of the system described herein, one or more of the interface devices 208-1 to 208-N, such as the device 208-3, may include one or more remote interface devices wireless coupled to the dialysis machine 102 via a sensor, such as the sensor 40, 140 or 140' discussed in FIG. 1 and/or FIG. 2. The remote interface device(s) 208-3 may include various embodiments and implementations of devices that may be used by a user (such as an HCP) in connection with the monitoring and/or control of the dialysis machine 102, as further discussed in detail elsewhere herein.

Figure 4:
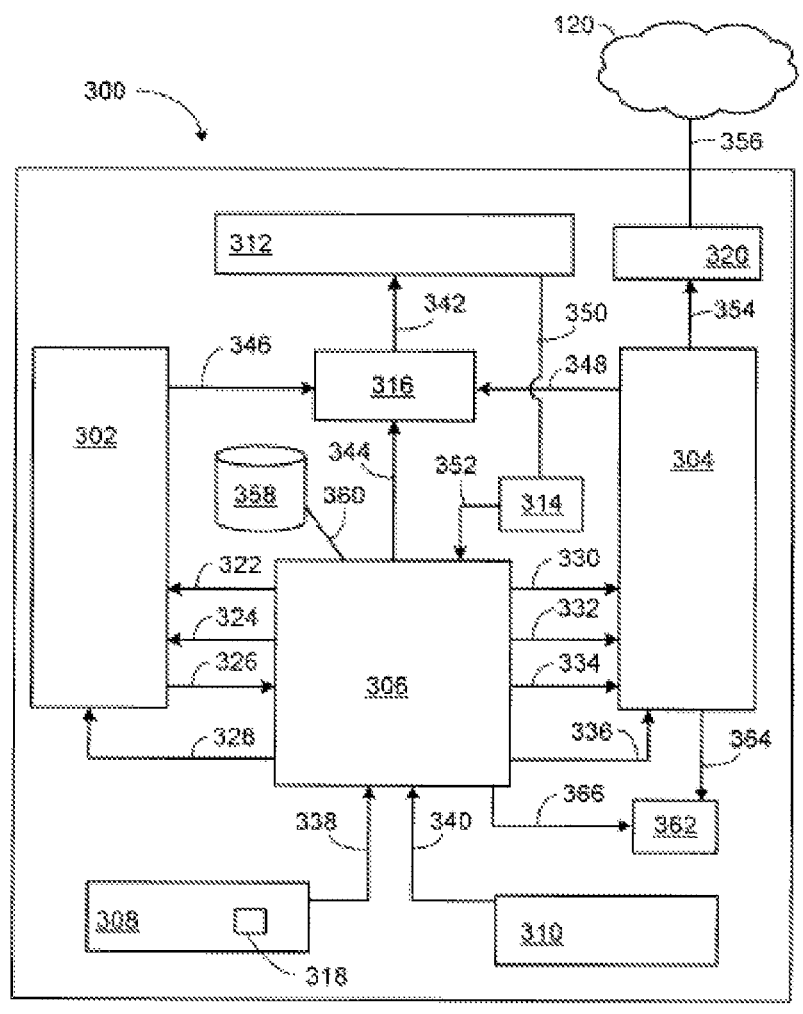
FIG. 4 is a schematic illustration of a more detailed implementation of the dialysis machine according to an embodiment of the system described herein.

FIG. 4 is a schematic illustration of a more detailed implementation 300 of the dialysis machine 102 according to an embodiment of the system described herein. A UIP 306 is configured to share user interface resources, e.g., a keyboard 308, a pointing device 310 (such as a touchpad), a display 312 with a touch screen, and/or a remote interface device 400, between a first processing device 302 and a second processing device 304. The first processing device 302 may be a functional dialysis processing device (FHP) 302 that may be configured to monitor dialysis functions of the HD device 300. The second processing device 304 may be a microprocessor, such as a standard personal computer (PC) processor, embedded within the HD device 300, and may be referred to as an embedded processing device (EP) 304. The FHP 302 is connected to the UIP 306 via connections 322, 324, 326, 328, and the EP 304 is connected to the UIP 306 via connections 330, 332, 334, 336.

The keyboard 308 is connected to the UIP 306 via connection 338. The pointing device 310 is connected to the UIP 306 via connection 340. The display 312 is connected to a digital video switch 316 via connection 342, which is in turn connected to the UIP 306, the FHP 302, and the EP 304 via respective connections 344, 346, 348. A touch screen controller 314 is connected to the display 312 via connection 350, and to the UIP 306 via connection 352. Although one UIP 306 is shown in FIG. 4, several user interface processing devices may be used to implement the functionality of the UIP 306. The UIP 306 is connected to memory 358 via a connection 360. Other memory (not shown) may be connected to, and, used by, e.g., the FHP 302 and/or the EP 304. The EP 304, for example, may utilize a flash memory rather than a conventional hard drive. The HD device 300 also includes an audio device 362. The audio device 362 is connected to the EP 304 via connection 364 and the UIP 306 via connection 366. FIG. 4 is intended to show functional connections between devices of the HD device 300, so more or fewer connections may be used than are shown in FIG. 4.

As described above, the UIP 306 may switch focus from the FHP 302 to the EP 304. The UIP 306 may likewise switch focus from the EP 304 to the FHP 302. When the FHP 302 has focus, one or more of the keyboard 308, the pointing device 310, the display 312 with a touch screen will generally affect operation of the FHP 302. When the EP 304 has focus, the keyboard 308, the pointing device 310, the display 312 with a touch screen, and/or the remote interface device 400 may generally affect operation of the EP 304. User interactions with the devices 308, 310, 312, 400 will likewise generally affect operation of whichever processing device (the FHP 302 or the EP 304) has focus. The processing device that has focus (the FHP 302 or the EP 304) may control, e.g., the display 312 in certain circumstances.

In various implementation, one or more of the user interface devices may be located external to the HD device 300. In this example implementation, when the EP 304 has focus, the FHP 302 does not have focus, and the FHP 302 may not have control of and/or be controlled by the devices 308, 310, 312, 400. When the FHP 302 has focus, the EP 304 does not have focus, and the EP 304 may not have control of and/or be controlled by the devices 308, 310, 312, 400. The UIP 306 may send protocol data relating to the devices 308, 310, 312 to the EP 304 and the FHP 302, even when one of these devices does not have focus, so that the EP 304 and the FHP 302 may maintain connections with the devices 308, 310, 312. That is, from the perspective of the processing device (EP 304 or FHP 302) that does not have focus, a connection at least appears to be maintained with the devices 308, 310, 312, 400, even though these devices 308, 310, 312, 400 are not controlled by, and do not control, the processing device that does not have focus. The UIP 306 may therefore send protocol data related to the devices 308, 310, 312, 400 to the FHP 302 and the EP 304, irrespective of which processing device 302, 304 has focus. The UIP 306 may switch between modes. The modes may be exclusive of one another and may include a mode in which the first processing device 302 has focus, and a mode in which the second processing device 304 has focus.

In accordance with the system described herein, it is noted that systems and techniques are known for enabling wearable displays, such as glasses, that may provide a controllable display to provide information and a controllable interface to a user wearing the display, and which are sometimes referred to as wearable "augmented reality" systems. For example, "Project Glass" is a research and development program by Google Inc. of Mountain View, Calif., to develop augmented reality head-mounted displays. Reference is made, for example, to U.S. Pat. No. 8,223,088 B1 to Gomez et al., entitled "Multimode Input Field for a Head-Mounted Display," and U.S. Pat. No. 8,228,315 B1 to Starner et al., entitled "Methods and Systems for a Virtual Input Device," both assigned to Google, Inc., that disclose systems for wearable displays and/or augmented reality systems. Other companies have also developed wearable displays and/or augmented reality systems (see, e.g., U.S. Patent App. Pub. No. 2012/0293548 A1 to Perez et al., entitled "Event Augmentation with Real-Time Information," assigned to Microsoft Corporation of Redmond, Wash., and U.S. Pat. No. 8,212,859 B2 to Tang et al., entitled "Peripheral Treatment for Head-Mounted Displays," assigned to Apple Inc. of Cupertino, Calif.). The system described herein may be used in connection with any appropriate wearable display and/or augmented reality system as implemented in accordance with the features and processing discussed herein.

Figure 5:
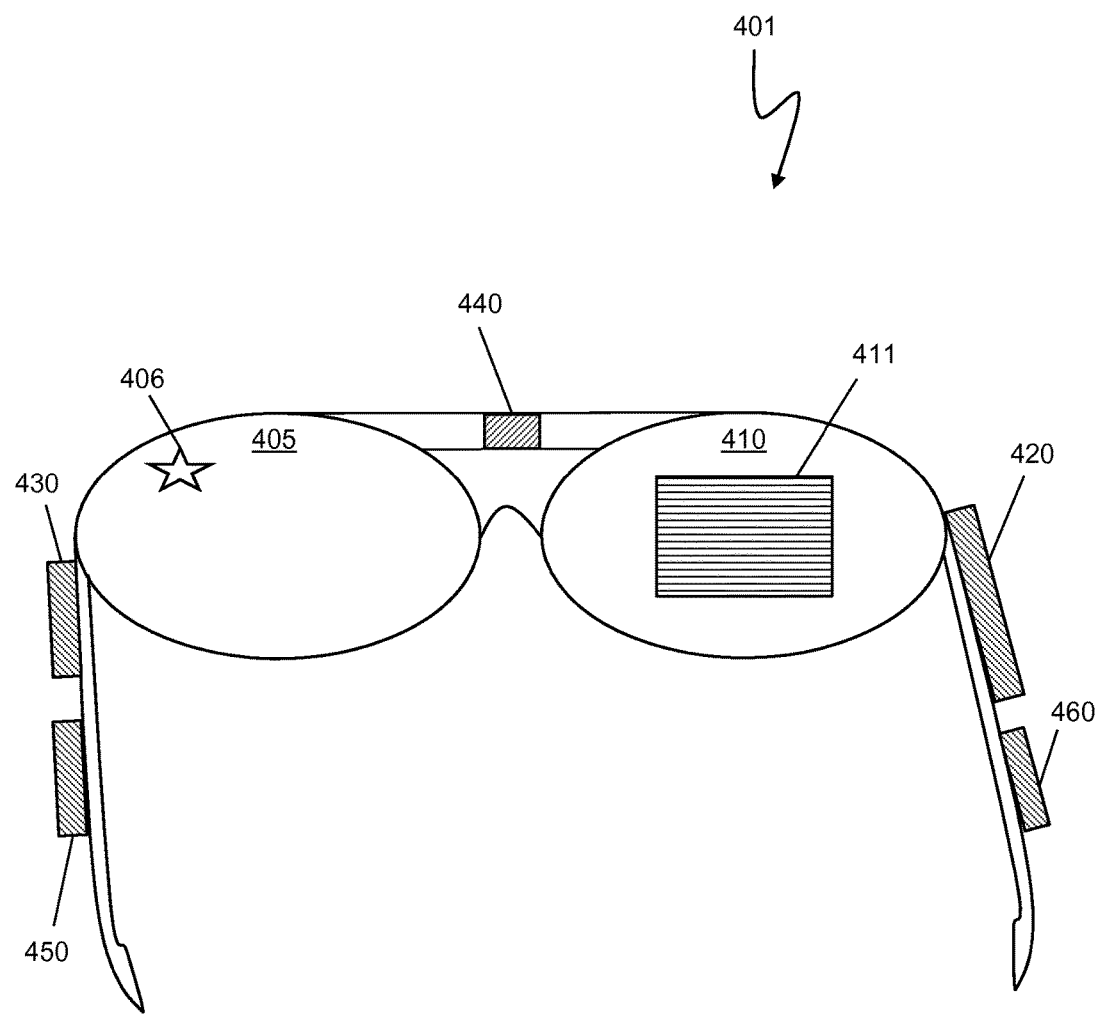
FIG. 5 is a schematic illustration of an interface device for a head-mounted display that may be a wearable augmented reality system and may be used in accordance with an embodiment of the system described herein.

FIG. 5 is a schematic illustration of an interface device 401 for a head-mounted display that may be a wearable augmented reality system and may be used in accordance with an embodiment of the system described herein. The interface device 401 may be an embodiment of the device 400 described in FIG. 4. The interface device 401 may be worn by a user, such as an HCP, in connection with remotely monitoring and/or controlling a dialysis machine or component, such as the dialysis machines 22, 102 and/or the controller device 30, during a dialysis treatment, as further discussed in detail elsewhere herein. The interface device is principally shown and described herein in connection with an implementation of the interface device as glasses. However, other head-mounted display implementation may be used in connection with the system described herein. Further, wearable implementations other than head-mounted displays may also be used in connection with the system described herein, including, for example, a wrist watch-style implementation.

The interface device 401 may include two sides with screens 405, 410 that may be used and function independently of each other. For example, in an embodiment, the screen 405 may be clear to enable a user to perform duties remote from the dialysis machine and unobstructed by any visual display during use of the interface device 401, and the screen 410 may display information 411 used in connection with monitoring and/or controlling the dialysis machine 102 and/or component thereof. Alternatively, for example, the screen 405 may include a symbol 406 that indicates an alert and is presented in a manner that does not obstruct a view through the interface device 401. In other embodiments, different types of information sent to, or generated by, the interface device 401 may be displayed on either of the screens 405, 410 and, when not in use, both of the sides may be transparent, for example.

In an embodiment, the interface device 401 may be communicationally paired with the dialysis machine 102 to provide that only the interface device 401 is wirelessly controlling the dialysis machine 102. The interface device 401 may receive certain information wirelessly transmitted by the sensor 140 or the sensor 140', for example, in connection with pairing or authenticating the interface device 401 with the dialysis machine 102, and/or in connection with acknowledging control signals sent by the interface device 401 to the dialysis machine 102 to control the display 112 thereof, as discussed herein. In an embodiment, the symbol 406 on the screen 405 may indicate a successful pairing of the interface device 401 with the dialysis machine 102. In other embodiments, the screen 405 may also display identification information in connection with the symbol 406 to help ensure the HCP is matching the patient being treated with the proper dialysis machine information being viewed on the interface device 401.

In an embodiment, the information 411 may be a screen similar to that being displayed on the display 112 of the dialysis machine 102 and/or may present other information in connection with the dialysis treatment and/or other functions performed by the HCP for monitoring and/or controlling the dialysis machine 102, as further discussed in detail elsewhere herein. In various other embodiments, the information 411 displayed on the interface device 401 may include an alert when the an alarm of the dialysis machine 102 is triggered, an alert when a patient requests help (nurse call), and/or an alert when the dialysis machine 102 nears the end of the dialysis treatment. Other types of information may also be displayed including, for example, presenting to the HCP a schedule of patients expected for the dialysis machine 102 for the day and/or an alert when a patient does not arrive as expected. According to the system described herein, in a clinical or dialysis setting, while an HCP is performing other duties, including duties for other patients, remote from the dialysis machine 102 and dialysis treatment being monitored by the HCP, using the interface device 401, the HCP may remotely monitor and control the dialysis treatment without having to physically contact the dialysis machine 102 and/or even without having to be physically present at the dialysis machine 102.

In an embodiment, in connection with the information 411 displayed on the interface device 401, the interface device 401 may receive information wirelessly transmitted by the sensor 140 or the sensor 140' and/or alternatively, may receive information wireless transmitted via the network 120, for example, acting as conduit for information received from the sensor 140, the sensor 140' and/or other component of the dialysis machine 102 that is then transmitted to the interface device 401 (see, e.g., FIG. 2). The interface device 401 may include a transceiver device 420 that receives and/or transmits signals according to the functionality discussed herein. The transceiver device 420 may include one or more processors to process the signals in connection with the display of the information 411 and in connection with the transmission of instructions for remotely controlling the dialysis machine 102. The transceiver device 420 may further include a memory, and/or other non-transitory computer-readable media, to store data in connection with the information transmitted and/or received by the interface device 401 and in connection with the execution of software or other executable code in connection with the operations of the interface device 401.

For example, the interface device 401 may include a command recognition device 430 that recognizes and interprets commands in connection with operation of the interface device 401, specifically in connection with selection, control and activation of elements on the screens 405, 410 of the interface device 401. In various embodiments, the commands may be gestures recognized and used by a gesture-recognition module of the command recognition device 430 in connection with the operation of the interface device 401 may include, for example, hand gestures, head gestures and/or eye gestures of the user. In other embodiments, the command recognition device 430 may include a voice recognition module that enables voice-based control of the interface device 401. The command recognition capability thereby enables hands-free, non-contact operation of the interface device and remote control of the dialysis machine according to the system described herein. Multiple techniques and systems are known for providing non-contact command recognition capability, including gesture and/or voice based command recognition, and reference is made, for purposes of illustrative and descriptive example only, to U.S. Pat. No. 8,228,315 to Starner et al., entitled "Methods and Systems for a Virtual Input Device," and U.S. Pat. No. 8,223,088 to Gomez et al., entitled "Multimode Input Field for a Head-Mounted Display," which are incorporated herein by reference.

The interface device 401 may further include a camera 440 that may be used in connection with capturing images that may be displayed and/or used by the interface device 401, as further discussed in detail elsewhere herein. In various embodiments, the camera 440 may also include video capabilities. It is noted that although the devices 420, 430 and 440 are shown as separate devices, in other embodiments, the functionalities of these devices may be incorporate into one integral device disposed on the interface device 401. Further, the interface device 401 may include a power source 450, such as a battery.

The interface device 401 may further include an audio input/output device 460 that may include a speaker component and a microphone component. The audio device 460 may enable the user to hear audible signals that may be transmitted by the sensor 40, 140 or 140'. For example, warning or alarm sounds of the dialysis machine 102 may be transmitted to interface 401 that are heard by the user via the audio device 460. In other embodiments the sensor 40, 140 or 140' may also include a speaker and/or a microphone component, such that an intercom-type verbal exchange may be enabled between the user wearing the interface device 401 and a patient at the dialysis machine 102. In various embodiments, the audio device 460 may also operate in connection with voice command recognition capability of the command recognition device 430, as further discussed elsewhere herein. It is also noted that the processing of the interface device 401 may enable the interface device to recognize a verbal communication from the patient that is then converted into text and displayed on one or more of the screens 405, 410. In connection therewith, the processing of the interface device 401 may enable translation capabilities. For example, a patient may make a verbal communication at the dialysis machine 102 in one language (such as Spanish) and the verbal communication is transmitted as a signal via the sensor 40, 140 or 140' to the interface device 401, where the verbal communication is converted into text and then translated into another language (such as English) via processing capabilities of the interface device 401 and the translated text displayed on one or more of the screens 405, 410 of the interface device 401.

Figure 6:
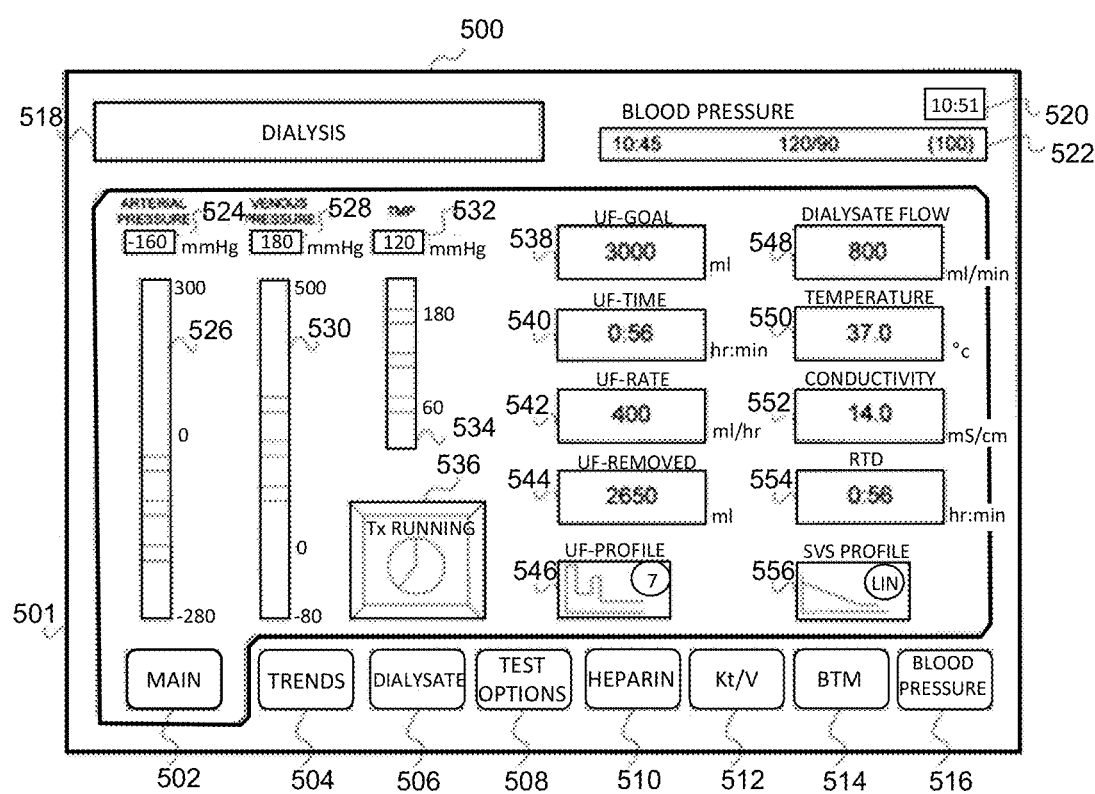
FIG. 6 is a schematic illustration showing an embodiment of information that may be displayed on the interface device according to an embodiment of the system described herein.

FIG. 6 is a schematic illustration showing an embodiment of information 500, like that discussed in connection with the information 411, that may be displayed on the interface device 401 according to an embodiment of the system described herein. The illustrated embodiment of the information 500 is presented by way of example only, and other information, particularly other operational functions and features for controlling and/or monitoring a dialysis treatment, may be displayed and/or controlled in accordance with the system described herein. In the illustrated embodiment, the information 500 may include a treatment screen in the display 112 of the dialysis machine 102 that incorporates the methods and systems for monitoring and/or controlling functions of the dialysis machine 102 that are discussed herein. Other systems and interfaces may also be used for controlling a dialysis machine and/or other medical device, and reference is made, for example, to U.S. Pat. No. 6,775,577 to Crnkovich et al., entitled "Method and System for Controlling a Medical Device," which is incorporated herein by reference.

Screen access buttons 502 (main access), 504 (trends), 506 (dialysate), 508 (test options), 510 (heparin), 512 (Kt/V), 514 (BTM), and 516 (blood pressure) may be used to access the various treatment screens in a manner that may be similar to that accessed at the display 112, for example, via touch screen functionality of the display 112. For example, as shown in FIG. 6, the main access button 502 has been activated using the interface device 401, revealing a main treatment access screen 501 that may be displayed on the interface device 401 and on the display 112 of the dialysis machine. It is noted that, in other embodiments, different and/or summarized versions of the information displayed on the display 112 of the dialysis machine 102 may be displayed on the interface device 401. A different treatment access screen may be displayed, for example, by pressing the different screen access buttons. The main treatment access screen 501 provides a general overview of the status of the current treatment. Other treatment screens may offer a more in-depth view of specific aspects of the current treatment, though some treatment screens may have some of the same information displayed as found on other treatment screens.

A status box 518 appears at the top left corner of the treatment screen being displayed in the information 500. During normal operation it displays the operation mode of the machine, which in this case is "Dialysis." During alarm situations, a warning message may be displayed in the status box 518. The message displayed in the status box 518 may also prompt the operator for a specific action in situations when the treatment parameters are being set. During normal treatment, a box 520 displays the current time and the box 522 displays the time of the last blood pressure reading and the patient's blood pressure and pulse rate at that time. Arterial pressure in mmHg is displayed numerically in a meter box 524, and graphically in a bar graph 526. Similarly, venous pressure in mmHg is displayed numerically in a meter box 528 and graphically in a bar graph 530, and transmembrane pressure (TMP) in mmHg is displayed numerically in a meter box 532 and graphically in a bar graph 534.

A Tx clock button 536 may be activated start, or to pause or suspend, the treatment. The Tx clock button 536 controls multiple functions of the hemodialysis machine when it is activated. A UF-goal button 538 displays the desired ultrafiltration (UF) in milliliters to be removed during the dialysis treatment. This is typically the difference between the patient's pre and dry weight plus saline or fluid intake during treatment. The UF-time button 540 acts as a countdown timer displaying the remaining time in hours and minutes that ultrafiltration will be performed. The timer stops during a blood alarm or whenever the UF pump is stopped. During treatment, A UF-rate button 542 displays the current rate of ultrafiltration in milliliters per hour. The rate ultrafiltration occurs is determined by the values entered in a UF-goal button 538 and a UF-time button 540 and the profile selected with a UF-profile button 546. A UF-removed button 544 keeps a running total in milliliters of the fluid drawn from the patient through ultrafiltration. When the value displayed in the UF-Removed button 544 is equal to the value entered in the UF-goal button 538, an alarm sounds and the message, "UF GOAL REACHED" is displayed in the status box 518. A UF-profile button 546 when touched brings up the UF Profile selection screen. Once a profile is selected, and the operator pushes the main access button 502, the profile selected is displayed in the UF-profile button 546.

A dialysate flow button 548 displays the current dialysate flow rate in milliliters per minute. A temperature button 550 displays the current temperature in degrees centigrade of the dialysate. Pressing the temperature button 550 allows the operator to set the desired temperature, and thereafter the actual temperature is displayed. If the temperature varies too far from the set point, an alarm sounds, a warning message is displayed in the status box 518, and the dialysate goes into bypass. A conductivity button 552 displays the current conductivity in millisiemens per centimeter of the dialysate. An RTD (Remaining Time of Dialysis) button 554 acts as a countdown timer displaying the amount of treatment time remaining. At the end of treatment (RTD=0:00) an alarm sounds and the message "RTD ZERO" is displayed in the status box 518. An SVS profile button 556 when touched brings up the Sodium Variation System (SVS) profile selection screen. Once a profile is selected, and the operator pushes the main access button 502, the profile selected is displayed in the SVS profile button 556.

In various embodiments, commands recognized by the interface device 401, such as gesture and/or voice commands, may be used to control functionality of the treatment screen being displayed as information 500 on the interface device 401. Accordingly, the mechanism of control of the treatment screen may deviate from control of the treatment screen that is being displayed on the display 112 of the dialysis machine 102. For example, whereas the display 112 on the dialysis machine 102 is controlled by touch screen functionality, treatment screen displayed on the screen 410 of the interface device 401 may be controlled, for example, by the command-based recognition that may be used to iterate through and/or highlight different buttons of the information 500 for the treatment screen that is being displayed on the screen 410. As discussed elsewhere herein, in other embodiments, the information 500 being displayed on the interface device 401 may present a treatment screen that is somewhat different from the treatment screen presented on the display 112 of the dialysis machine 102 in a manner that facilitates that command-based recognition control enabled by the interface device 401.

Figure 7:
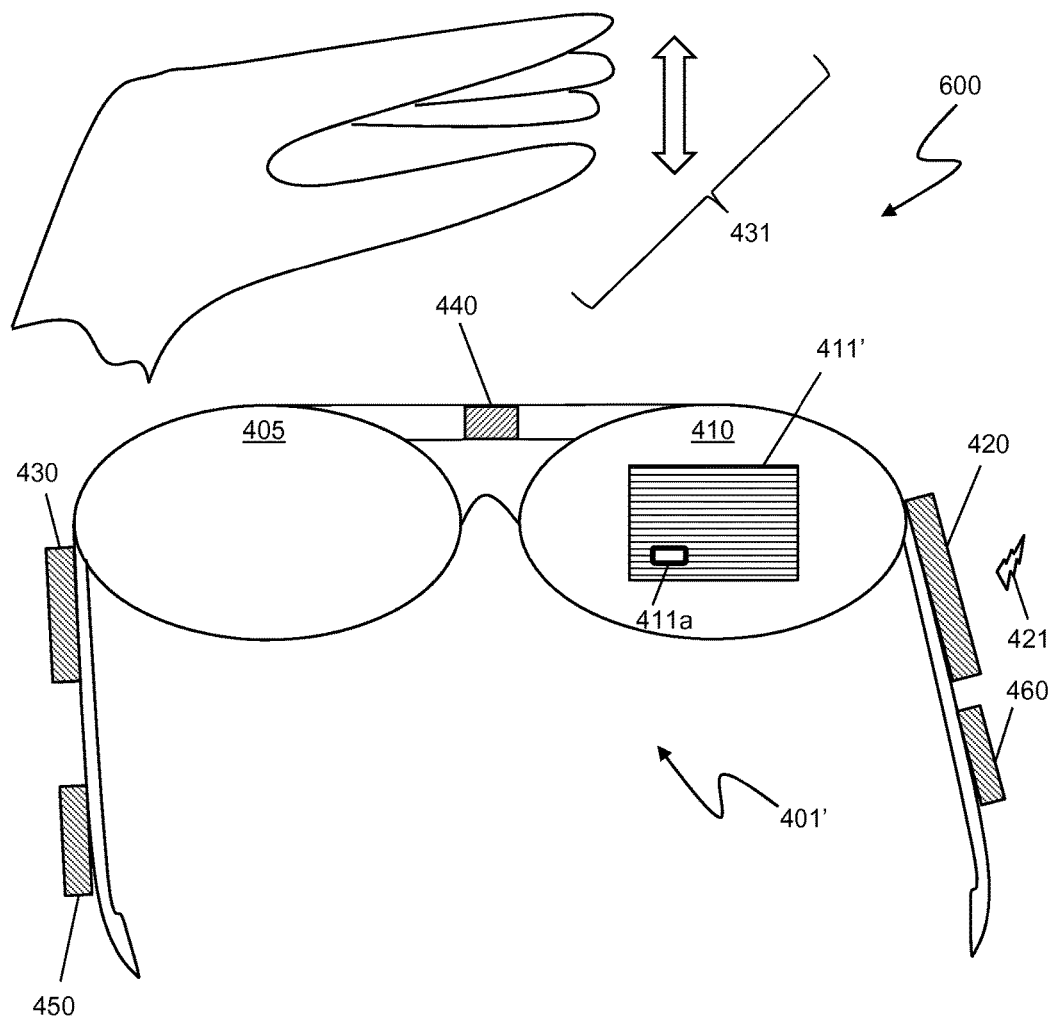
FIG. 7 is a schematic illustration showing a gesture by a user that may be used to control an interface device according to an embodiment of the system described herein.

FIG. 7 is a schematic illustration 600 showing a gesture 431 by a user that may be used to control an interface device 401', that is like the interface device 401 and having similar components thereof but showing a different operational state, according to an embodiment of the system described herein. The screen 410 of the interface device 401' shows information 411' in which a section 401a has been activated by the gesture 431, as recognized by the command recognition device 430. The activated section 401a may be a button, such as the main access button 502 (see FIG. 6) that activates the providing of a main access treatment screen 501 to provide a general overview of the status of a current dialysis treatment being performed. The providing of the main access treatment screen 501 may be performed by the activation instruction of the button 401a being processed by the transceiver device 420 and wirelessly transmitted via a signal 421 to the sensor 140 of the dialysis machine and/or the sensor 140' either directly or via the network 120 (see FIG. 2). Updated information concerning the result of the activated section 401a, such as the information for the main access treatment screen 501, may be wirelessly transmitted to the interface device 401' from the dialysis machine 102, which is used by the transceiver device 420 to update the screen 410 with updated information.

Figure 8:
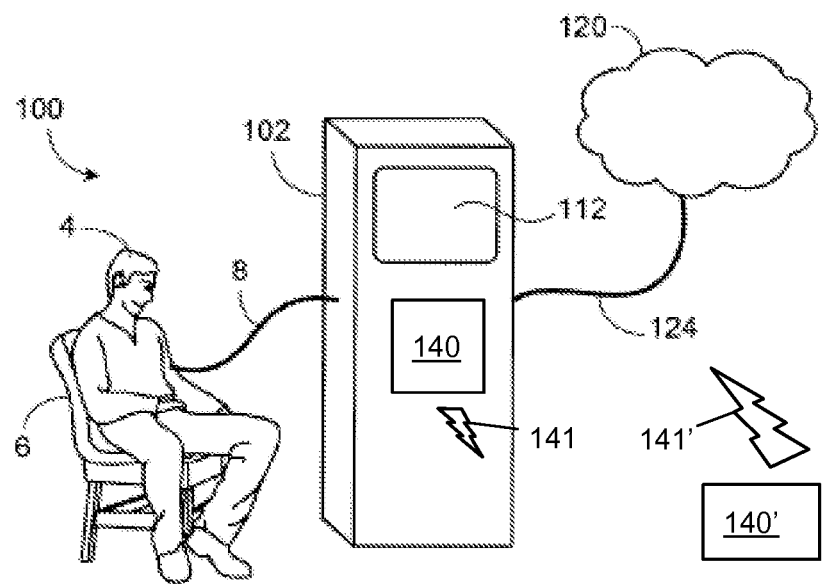
FIG. 8 is a schematic illustration showing a health care practitioner (HCP) wearing the interface device in connection with the monitoring and/or control of a dialysis treatment being performed in the patient care environment.
Figure 8:
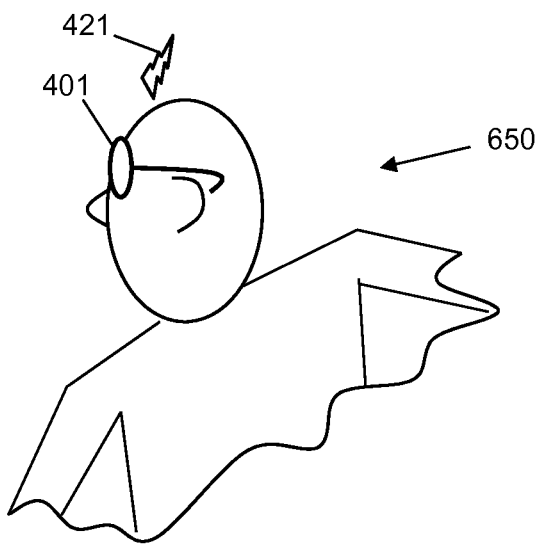

FIG. 8 is a schematic illustration showing an HCP 650 wearing the interface device 401 in connection with the monitoring and/or control of a dialysis treatment being performed in the patient care environment 100 (see, e.g., FIG. 2). The interface device 401 enables the HCP 650 to remotely monitor and/or control the dialysis machine 102 during the dialysis treatment. Information is exchanged among the interface device 401 and the dialysis machine 102 in a manner as discussed elsewhere herein, and particularly including wireless signal transfers, shown schematically as signals 421 from the interface device 401 and signal 141 or signal 141' from the sensor 140 or the sensor 140', respectively. It is noted that the signals 421, 141 and 141' are shown schematically and may also include the transfer of information via components of the network 120. Using the interface device 401, the HCP 650 may remotely receive alerts and/or other information during the dialysis treatment and may remotely control the dialysis machine 102 using, for example, gestures and/or voice in a manner that enables the HCP 650 to control, remotely from the patient care environment 100, the dialysis machine 102 without being in a visual line-of-sight with the dialysis machine 102, and, of course, without having to touch the dialysis machine 102. The system described herein advantageously enables the HCP 650 to perform other duties while also monitoring and/or controlling the dialysis machine 102.

Figure 9:
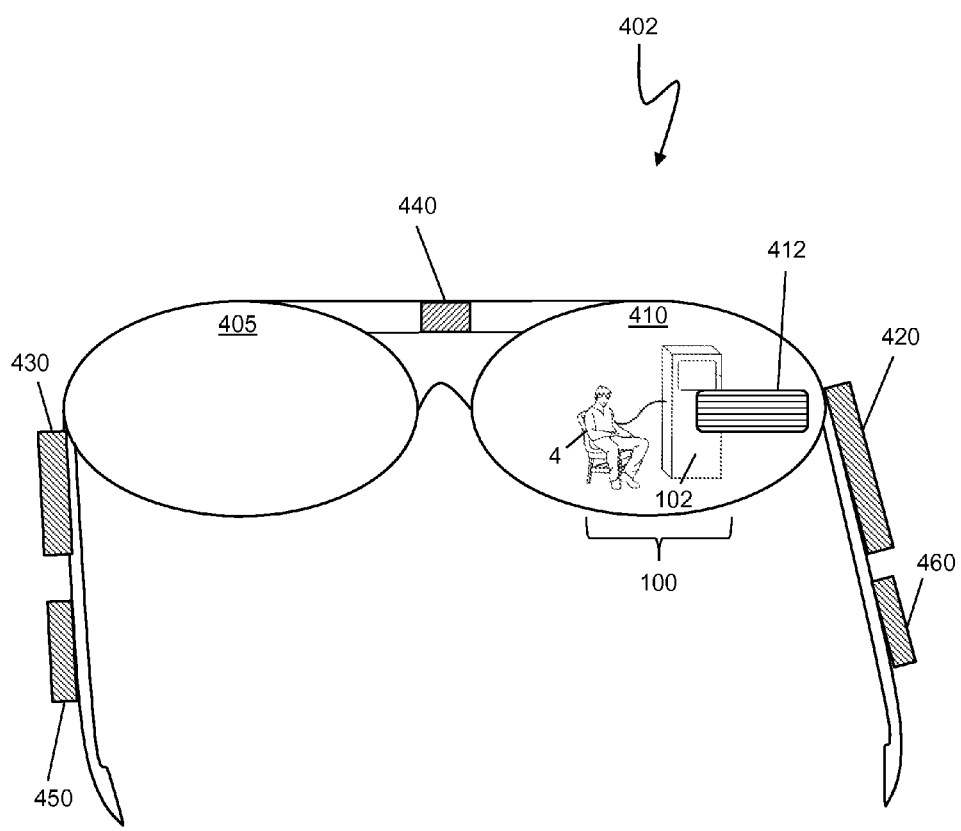
FIG. 9 is a schematic illustration of an interface device in which the patient care environment is being viewed by the HCP through the interface device according to an embodiment of the system described herein.

FIG. 9 is a schematic illustration of an interface device 402', similar to the interface device 401, that is like the interface device 401 and having similar components thereof but showing a different functionality and/or operational state, in which the patient care environment 100 is being viewed by the HCP through the interface device 401' according to an embodiment of the system described herein. In connection with augmented reality capabilities of the interface device 402, information 412 displayed on the interface device 402 may be shown in connection with the real time viewing of the patient care environment 100. For example, the information 412 may display the station number of the dialysis machine 102 and/or may display patient information of the patient 4, such as patient name, age and/or other patient information (e.g., birthdays, etc.). In other embodiments, the interface device 402 may be used to document real-time events in connection with treatment, such as emergencies and/or rare or abnormal alarm conditions.

Figure 10:
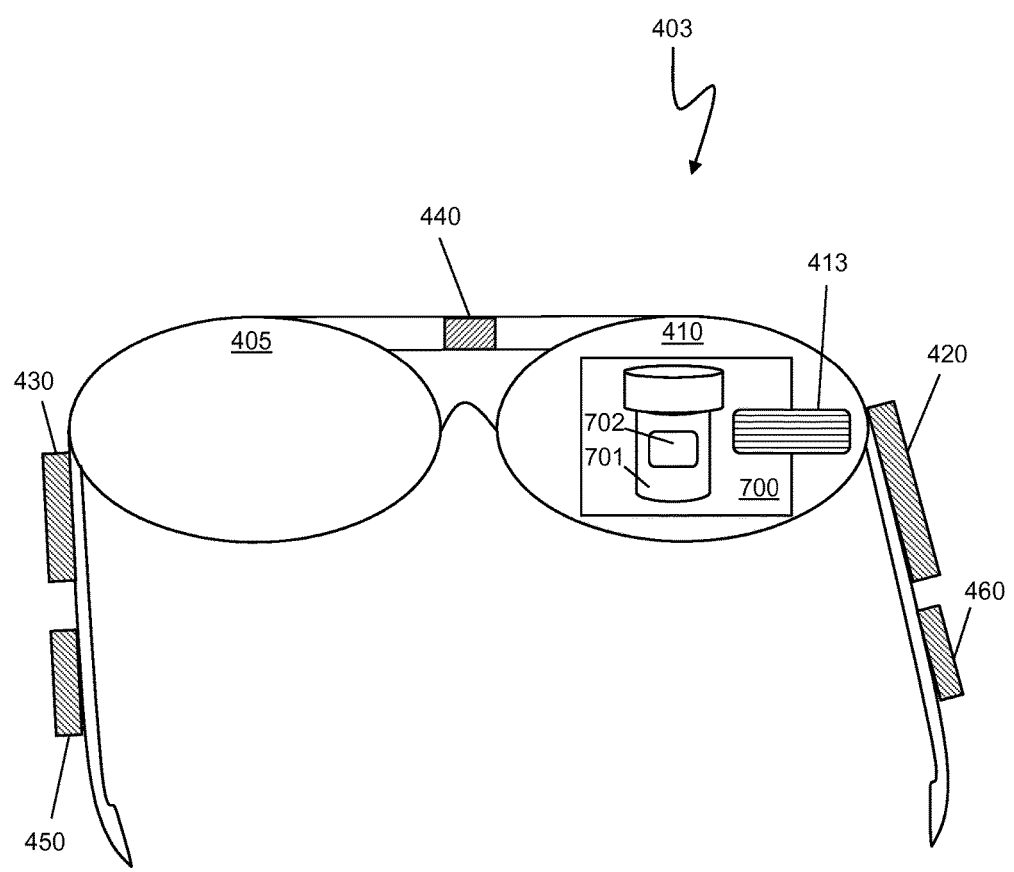
FIG. 10 is a schematic illustration of an interface device in which an image has been captured by a camera of the interface device and displayed on the screen of the interface device according to an embodiment of the system described herein.

FIG. 10 is a schematic illustration of an interface device 403, that is like the interface device 401 and having similar components thereof but showing a different functionality and/or operational state, in which an image 700 has been captured by the camera 440 of the interface device 403 and displayed on the screen 410 of the interface device 403 according to an embodiment of the system described herein. Information 413 concerning the image 700 may be displayed on the screen 410 of the interface device 401. For example, the image 700 may be of items, supplies and/or medications, such as item 701, and the interface device 403 may be used to document the items, supplies and/or medications. In other embodiments, the information 413 displayed on the interface device 403 may include alerts or warnings concerning the item 701 in the image 700. In an embodiment, the item 701 may include a matrix or 2D bar code 702 (such as a Quick Response (QR) code) that may be captured by the camera 440 and processed by the interface device 403.

Figure 11:
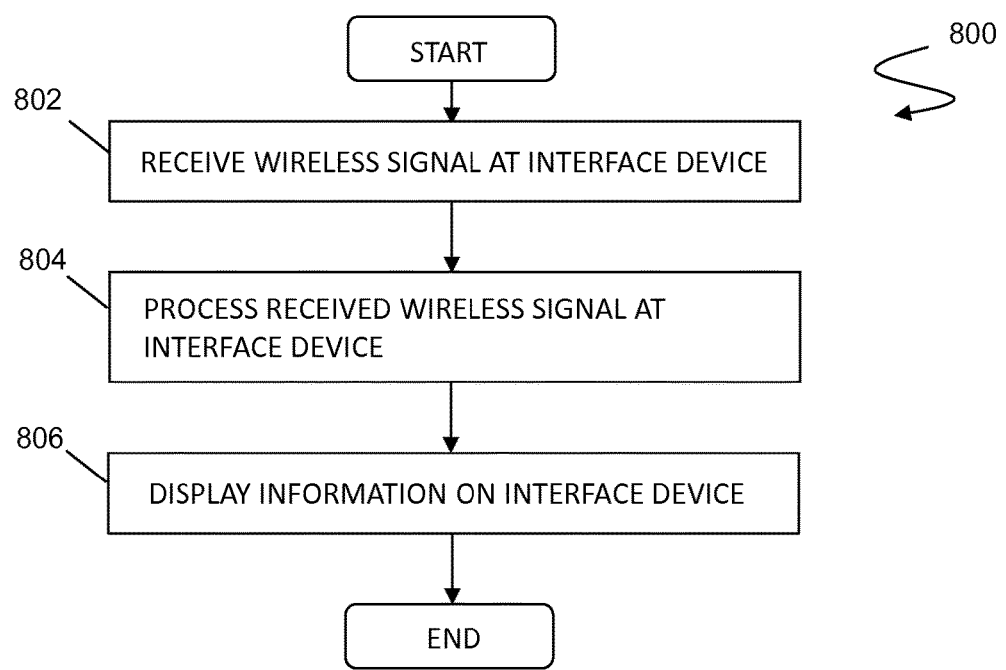
FIG. 11 is a flow diagram showing processing steps in connection with receipt and display of information on an interface device according to an embodiment of the system described herein.

FIG. 11 is a flow diagram 800 showing processing steps in connection with receipt and display of information on an interface device, like that described herein, for example, in connection with the interface device 401, 401', 402 or 403, according to an embodiment of the system described herein. At a step 802, the interface device receives a wireless signal, transmitted, for example, from a dialysis machine, like the dialysis machine 22 or 102, that is performing a dialysis treatment on a patient. The interface device may be worn by a user, such as an HCP who is remotely monitoring the dialysis treatment. After the step 802, processing proceeds to a step 804 where the wireless signal is processed by one or more components of the interface device. In an embodiment, the processing of the wireless signal may be in connection with information of the dialysis treatment, including treatments screens and/or other information of the dialysis treatment and/or the dialysis machine.

After the step 804, processing proceeds to a step 806 where processed information from the wireless signal is displayed on a display of the dialysis device in connection with navigation of information displayed on the screens of the dialysis device. After the step 806, processing is complete for the described processing iteration of the interface device and dialysis device. It is noted that the processing of the flow diagram 800 may be an on-going process in which the interface device repeatedly transmits wireless signals in response to user actions which are then repeatedly received by the dialysis machine. It is noted that the processing steps performed in the flow diagram 800 may be performed in connection with the execution of software on a non-transitory computer-readable medium of the interface device by one or more processors of the interface device. In an embodiment, the software may correspond to software that facilitates and/or otherwise interfaces with the dialysis machine in connection with the performance of the dialysis treatment, such as by providing one or more dialysis treatment screens.

Figure 12:
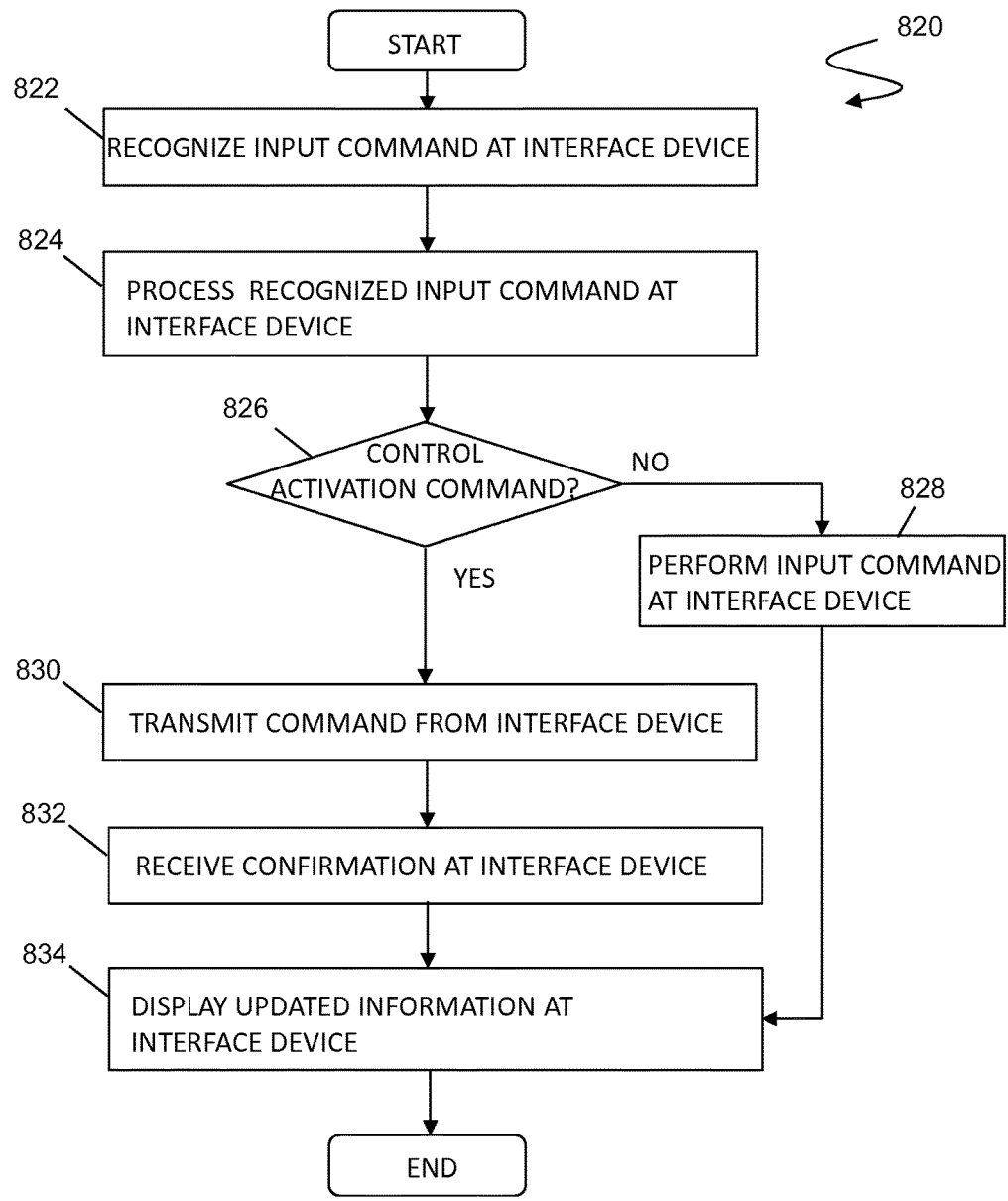
FIG. 12 is a flow diagram showing processing steps in connection with command recognition and information transmission in connection with the use of an interface device, like that described herein, for example, in connection with the interface device, according to an embodiment of the system described herein.

FIG. 12 is a flow diagram 820 showing processing steps in connection with command recognition and information transmission in connection with the use of an interface device, like that described herein, for example, in connection with the interface device 401, 401', 402 or 403, according to an embodiment of the system described herein. For example, in an embodiment, the processing of the flow diagram 820 may follow the processing of the flow diagram 800. At a step 822, one or more components of the interface device recognizes a input command by the user (HCP) who is wearing the interface device. In various embodiments, the input command may be a gesture and/or a voice command that is recognized by the one or more components of the interface device. After the step 822, processing proceeds to a step 824 where the input command recognized by the interface device is processed in connection with the information being displayed on the display screen of the interface device.

After the step 824, processing proceeds to a test step 826 where it is determined whether the input command corresponds to a control activation of one or more parts of the information being displayed on the interface device that requires transmission from the interface device. For example, the control activation may be in connection with a button being displayed on the interface device. If, at the test step 826, it is determined that the input command is not a control activation command that requires transmission, then processing proceeds to a step 828 where the input command is performed at the interface device. For example, in various embodiments, the input command may correspond to scrolling through multiple screens of the information being displayed on the interface device and/or may correspond to the capturing of an image by a camera component of the interface device. After the step 828, processing proceeds to a step 834 where updated information is displayed on the interface device.

If, at the test step 826, it is determined that input command corresponds to a control activation command that involves transmission of a wireless signal from the interface device, then processing proceeds to a step 830 where the input command is wirelessly transmitted from the interface device. For example, the control activation command may involve activation of a button that controls the dialysis machine and/or dialysis treatment that is being performed and which is being remotely monitored by the HCP wearing the interface device. In such a case, the input command is being wirelessly transmitted to the dialysis machine to control the treatment, such as to adjust a parameter of the dialysis treatment and/or to stop the dialysis treatment, for example. After the step 830, processing proceeds to a step 832 where the interface device receives a confirmation that the control activation command has been received and processed by the dialysis machine. The confirmation may be in the form of updated information transmitted to the interface device in processing like that discussed in connection with the flow diagram 800. After the step 832, processing proceeds to the step 834, where updated information is displayed on the interface device. The updated information displayed on the interface device may indicate appropriate processing of the control activation command at the dialysis machine.

After the step 834, processing is complete for the described processing iteration of the interface device. It is noted that the processing of the flow diagram 820 may be an on-going process in which the interface device continuously monitors for processes for receipt of input commands. It is noted that the processing steps performed in the flow diagram 820 may be performed in connection with the execution of software on a non-transitory computer-readable medium of the interface device by one or more processors of the interface device.

In an embodiment, the software may correspond to software that facilitates and/or otherwise interfaces with the dialysis machine in connection with the performance of the dialysis treatment, such as by providing one or more dialysis treatment screens.

Figure 13:
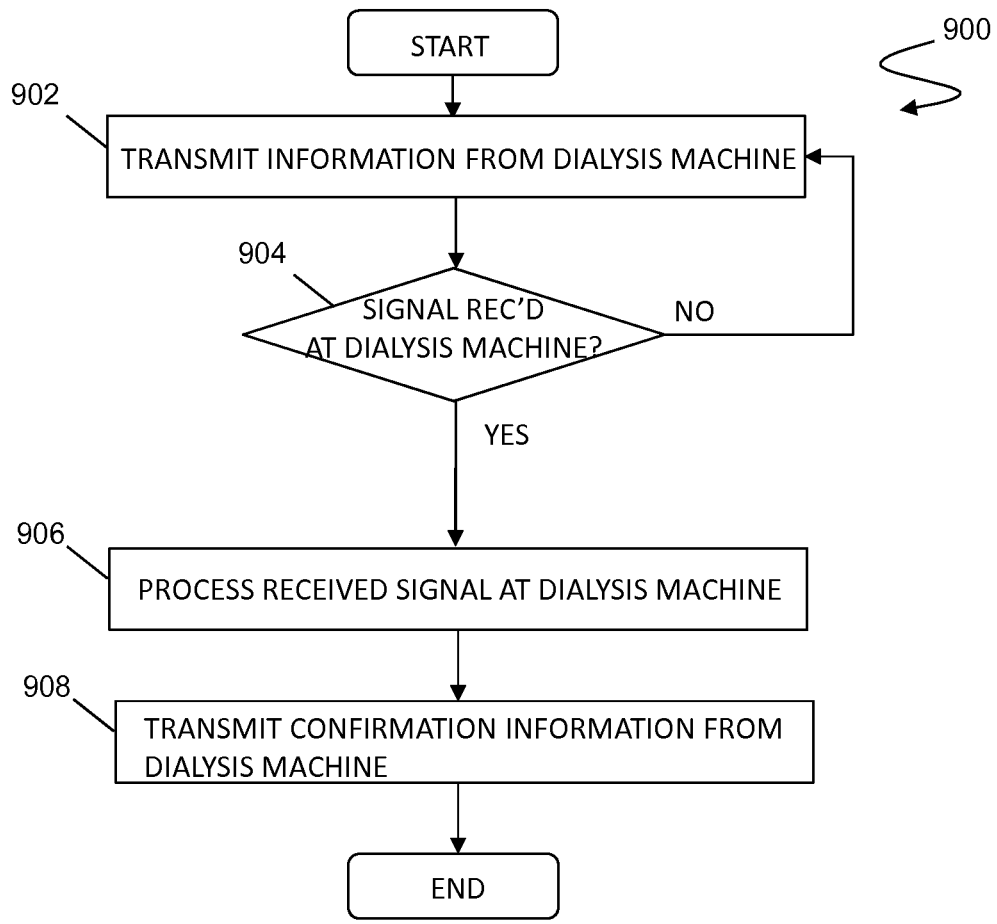
FIG. 13 is a flow diagram showing processing in connection with wirelessly transmitting and/or receiving information from a dialysis machine in connection with a dialysis treatment according to an embodiment of the system described herein.

FIG. 13 is a flow diagram 900 showing processing in connection with wirelessly transmitting and/or receiving information from the dialysis machine in connection with the dialysis treatment according to an embodiment of the system described herein. In various embodiments, a sensor of the dialysis machine, like that of the sensor 40, 140 or 140' discussed herein, may process wireless signals received and/or transmitted in connection with the operation of the dialysis machine and/or dialysis treatment. At a step 902, information of a dialysis treatment being performed by the dialysis machine is wirelessly transmitted from the dialysis machine. In various embodiments, the wireless transmission may include direct broadcast from the sensor of the dialysis machine and/or may include use of one or more components of a network (see, e.g., FIG. 2). After the step 902, processing proceeds to test step 904 where it is determined whether a wireless signal has been received at the dialysis machine. For example, the wireless signal may be received from an interface device, like the interface device 401, 401', 402 or 403, in connection with processing like that discussed in connection with the flow diagram 820. If no wireless signal has been received at the test step 904, processing returns to the step 902.

If, at the test step 904, it is determined that a wireless signal has been received, then processing proceeds to a step 906 where the received wireless signal is processed. In various embodiments, the received wireless signal may be a control activation command received from an interface device, like that interface device 401, 401', 402 or 403, in connection with the remote control of the dialysis machine by a user (HCP) wearing the interface device. After the step 906, processing proceeds to a step 908 where the dialysis machine, e.g., via the sensor 40, 140 or 140', transmits a wireless signal that confirms receipt and processing of the received control activation command. For example, the received control activation command may have adjusted a parameter of the dialysis treatment being performed and the confirmation is updated information of the dialysis treatment that is transmitted to the interface device. The updated information may therefore correspond to a treatment screen of the dialysis treatment displayed on the dialysis machine.

After the step 908, processing is complete for the described processing iteration of the interface device. It is noted that the processing of the flow diagram 900 may be an on-going process in which the dialysis continuously processes monitors for input commands and/or signals in connection with the system described herein. It is noted that the processing steps performed in the flow diagram 900 may be performed in connection with the execution of software on a non-transitory computer-readable medium of the dialysis machine by one or more processors of the dialysis machine, including, in particular, one or more processors of a sensor of the dialysis machine. In an embodiment, the software may correspond to software that facilitates and/or otherwise interfaces with an interface device specifically in connection with remote monitoring and/or control of the dialysis treatment, such as in connection with the providing of dialysis treatment screens. It is noted that the processing of the flow diagram 900 may be performed in conjunction with other processing of the dialysis machine, including for example, input of commands directly to the dialysis machine via a touch screen display, for example.

It is noted that the system described herein is discussed principally in connection with the use of dialysis machines and treatments. It is noted that, in other embodiments, the system described herein may also be used in connection with other medical devices where monitoring and/or control of such devices may be appropriately performed remotely. It is also noted that the system described herein may be used in connection and conjunction with the features and functions of a system like that described in US Publication No. 2014/0267003 A1 to Wang et al., entitled "Wireless Controller to Navigate and Activate Screens on a Medical Device," which is assigned to the same assignee as that of the present application and which is incorporated herein by reference.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of remotely interfacing with a medical device, comprising:
    providing a wearable interface device that enables remote interfacing with the medical device by a user wearing the wearable interface device, wherein the wearable interface device includes a command recognition device that recognizes and interprets commands in connection with operation of the wearable interface device, and wherein the wearable interface device includes a first screen for displaying information and a second screen for displaying information that provides a view through the wearable interface device that is unobstructed by a visual display during use of the wearable medical device, wherein the second screen functions independently of the first screen and wherein information corresponding to treatment being performed is displayed on the first screen and an alert symbol is displayed on the second screen, the alert symbol remotely alerting the user that the medical device is near an end of the treatment being performed;
    providing a display on the medical device, wherein the display includes touch screen features that accept commands for controlling the medical device;
    wirelessly exchanging signals between the wearable interface device and the medical device, wherein the signals correspond to a treatment performed using the medical device and wherein at least one processing device of the medical device that is processing signals received from the wearable interface device is given focus to enable the wearable interface device to control the medical device via the at least one processing device in a mode that excludes control of the medical device by other devices different from the wearable interface device while the signals are being processed;
    processing at least one of the signals at the wearable interface device to generate information corresponding to the treatment performed using the medical device;
    displaying the information on at least one of the first screen and the second screen of the wearable interface device; and
    recognizing, using the command recognition device, at least one non-contact gesture input by the user, wherein control of treatment using the wearable interface device is different from control of treatment using the touch screen of the medical device.

2. The method according to claim 1, wherein the medical device includes a dialysis machine.

3. The method according to claim 1, wherein the non-contact command is used to remotely control the medical device during the treatment.

4. The method according to claim 3, wherein the non-contact command includes a command to remotely control the medical device during the treatment by modifying at least one parameter of the medical device from a position in which the wearable interface device is out of a visual line-of-sight of the medical device.

5. The method according to claim 1, wherein the wearable interface device is a head-mounted device and wherein the information displayed on the first screen of the wearable interface device includes dialysis treatment information.

6. The method according to claim 5, wherein the dialysis treatment information includes an alert concerning the dialysis treatment.

7. The method according to claim 5, further comprising:
augmenting a real view through the wearable interface device with information corresponding to the dialysis treatment information.

8. The method according to claim 1, wherein the at least one non-contact gesture input by the user includes hand gestures, head gestures and eye gestures of the user.

9. A non-transitory computer-readable medium storing software that remotely interfaces with a medical device, the software comprising:
executable code that operates a wearable interface device that enables remote interfacing with the medical device by a user wearing the wearable interface device, wherein the wearable interface device includes a command recognition device that recognizes and interprets commands in connection with operation of the wearable interface device, and wherein the wearable interface device includes a first screen for displaying information and a second screen for displaying information that provides a view through the wearable interface device that is unobstructed by a visual display during use of the wearable medical device, wherein the second screen functions independently of the first screen and wherein information corresponding to treatment being performed is displayed on the first screen and an alert symbol is displayed on the second screen, the alert symbol remotely alerting the user that the medical device is near an end of the treatment being performed;
executable code that operates a display on the medical device, wherein the display includes touch screen features that accept commands for controlling the medical device;
executable code that wirelessly exchanges signals between the wearable interface device and the medical device, wherein the signals corresponds to a treatment performed using the medical device and wherein at least one processing device of the medical device that is processing signals received from the wearable interface device is given focus to enable the wearable interface device to control the medical device via the at least one processing device in a mode that excludes control of the medical device by other devices different from the wearable interface device while the signals are being processed;
executable code that processes at least one of the signals at the wearable interface device to generate information corresponding to the treatment performed using the medical device;
executable code that displays the information on at least one of the first screen and the second screen of the wearable interface device; and
executable code that recognizes, using the command recognition device, at least one non-contact gesture input by the user, wherein control of treatment using the wearable interface device is different from control of treatment using the touch screen of the medical device.

10. The non-transitory computer-readable medium according to claim 9, wherein the medical device includes a dialysis machine.

11. The non-transitory computer-readable medium according to claim 9, wherein the non-contact command is used to remotely control the medical device during the treatment.

12. The non-transitory computer-readable medium according to claim 11, wherein the non-contact command includes a command to remotely control the medical device during the treatment by modifying at least one parameter of the medical device from a position in which the wearable interface device is out of a visual line-of-sight of the medical device.

13. The non-transitory computer-readable medium according to claim 9, wherein the wearable interface device is a head-mounted device, and wherein the information displayed on the first screen of the wearable interface device includes dialysis treatment information.

14. The non-transitory computer-readable medium according to claim 13, wherein the dialysis treatment information includes an alert concerning the dialysis treatment.

15. The method according to claim 13, wherein the software further comprises:
executable code that augments a real view through the wearable interface device with information corresponding to the dialysis treatment information.

16. The non-transitory computer-readable medium according to claim 9, wherein the at least one non-contact gesture input by the user includes hand gestures, head gestures and eye gestures of the user.

17. A system for enabling remote interfacing with a medical device, comprising:
at least one processing device of the medical device that receives and transmits signals corresponding to a medical treatment performed by the medical device;
a display on the medical device, wherein the display includes touch screen features that accept commands for controlling the medical device;
a wearable interface device that is worn by a user and that is wirelessly coupled to the at least one processing device of the medical device, wherein the at least one processing device of the medical device is given focus to enable the wearable interface device to control the medical device via the at least one processing device in a mode that excludes control of the medical device by other devices different from the wearable interface device while the signals are being processed and wherein the wearable interface device includes:
at least one processor that processes received signals into information corresponding to the medical treatment and transmits signals used to control the medical device;

a first screen for displaying information;

a second screen for displaying information that provides a view through the wearable interface device that is unobstructed by a visual display during use of the wearable medical device, wherein at least one screen of the first screen and the second screen displays the information corresponding to the medical treatment, wherein the second screen functions independently of the first screen and wherein information corresponding to treatment being performed is displayed on the first screen and an alert symbol is displayed on the second screen, the alert symbol remotely alerting the user that the medical device is near an end of the treatment being performed; and at least one command recognition device that recognizes a non-contact gesture input by the user to the wearable interface device, wherein control of treatment using the wearable interface device is different from control of treatment using the touch screen of the medical device.

18. The system according to claim 17, wherein the wearable interface device further includes:

a camera that captures an image being viewed using the wearable interface device.

19. The system according to claim 17, wherein the wearable interface device controls the medical device when the wearable interface device is out of a visual line-of-sight with the medical device during the medical treatment.

20. The system according to claim 17, wherein the first screen and the the second screen are part of a head-mounted display of the wearable interface device, and wherein the wearable interface device includes a non-transitory computer readable medium storing software that enables control of the medical device during the medical treatment using at least one treatment display displayed on at least of the first screen and the second screen of the head-mounted display.

21. The system according to claim 17, wherein the medical device includes a dialysis machine.

22. The system according to claim 17, wherein the non-contact gesture input by the user includes hand gestures, head gestures and eye gestures of the user.

* * * * *